(12) United States Patent
Sebastian et al.

(10) Patent No.: US 6,603,003 B2
(45) Date of Patent: Aug. 5, 2003

(54) METHOD FOR THE PREPARATION OF PIPERAZINE AND ITS DERIVATIVES

(75) Inventors: Sonny Sebastian, Hyderabad (IN); Hetal Virendra Patel, Baroda (IN); Rajamannar Thennati, Baroda (IN)

(73) Assignee: Sun Pharmaceutical Industries LTD, Mumbia (IN)

( * ) Notice: Subject to any disclaimer, the term of this patent is extended or adjusted under 35 U.S.C. 154(b) by 0 days.

(21) Appl. No.: 10/037,309

(22) Filed: Oct. 25, 2001

(65) Prior Publication Data

US 2002/0095038 A1 Jul. 18, 2002

(30) Foreign Application Priority Data

Jun. 29, 2001 (IN) .................... 994/MUM/2000

(51) Int. Cl.⁷ .................... C07D 241/04; C07D 487/14
(52) U.S. Cl. .................... 544/403; 544/404; 540/578
(58) Field of Search .................... 544/403, 404; 540/578

(56) References Cited

U.S. PATENT DOCUMENTS

| | | | |
|---|---|---|---|
| 4,062,848 A | * 12/1977 | Van Der Burg | |
| 4,772,705 A | 9/1988 | Schmiesing | |
| 4,912,110 A | 3/1990 | Lafon | |
| 5,414,087 A | 5/1995 | Speranza et al. | |

FOREIGN PATENT DOCUMENTS

| | | |
|---|---|---|
| CN | 1106000 | 8/1995 |
| JP | 49010513 | 3/1974 |
| JP | 58035179 | 3/1983 |
| SU | 467073 | 4/1974 |
| SU | 427936 | 5/1974 |
| WO | WO 98/08826 | 3/1998 |

OTHER PUBLICATIONS

Ogawa, Chemical Abstracts, vol. 98, No. 107317, Abstract for JP 57062268, Apr. 15, 1982.*

"Derivatives of Piperazine. XXXV. Synthesis of 2–Phenylpiperazine and Some Derivatives," by William R. Roderick, Howard J. Platte, and C. B. Pollard. J. Medical Chemistry, Mar. 1996.

"Agents Acting on CNS: Part XXV—2–Substituted 1,2,3,4,6,7,8,12b–Octahydropyrazino[2,I–a][2]benzazepines," by V. M. Dixit, J. M. Khanna & Nitya Anand. Indian Journal of Chemistry, vol. 14B, Nov. 1976, pp. 874–878.

* cited by examiner

Primary Examiner—Emily Bernhardt
(74) Attorney, Agent, or Firm—Proskauer Rose LLP

(57) ABSTRACT

A novel method for the synthesis of piperazine and its derivatives of formula 1,

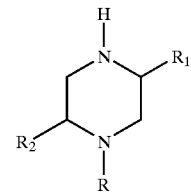

wherein R is selected from hydrogen, or a lower alkyl group having 1 to 6 carbon atoms or a phenylalkyl group the alkyl of which has 1 to 4 carbon atoms;

$R_1$ is selected from hydrogen, a methyl group, a phenyl group optionally substituted with an alkyl group having 1 to 6 carbon atoms, or a phenylalkyl group the alkyl of which has 1 to 4 carbon atoms; and $R_2$ is selected from hydrogen, or a methyl group, or a fluoromethyl group;

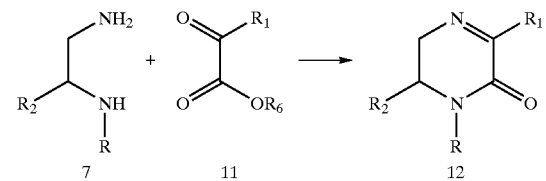

comprising the steps:

a. reacting an ester of formula 11 with substituted or unsubstituted ethylenediamine of formula 7 to give 3,4-dehydropiperazine-2-one and its derivatives of formula 12, wherein R, $R_1$, $R_2$ are as defined above and $R_6$ is a $C_1$ to $C_4$ linear or branched alkyl group; and b. reacting the 3,4-dehydro-piperazine-2-one and its derivatives of formula 12 with a reducing agent to yield the piperazine and its derivatives of formula 1.

11 Claims, No Drawings

METHOD FOR THE PREPARATION OF PIPERAZINE AND ITS DERIVATIVES

RELATED APPLICATION

This application is related to and claims the benefit of International Application No. PCT/IN01/00129, filed Jun. 29, 2001, published in English under PCT Article 21(2) as International Publication No. WO02/38552 A1 on May 16, 2002.

BACKGROUND OF THE INVENTION

The present invention relates to a novel method for the synthesis of piperazine and its derivatives of formula 1,

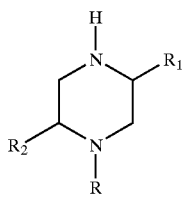

1 wherein R is selected from hydrogen or a lower alkyl group having 1 to 6 carbon atoms or a phenylalkyl group the alkyl of which has 1 to 4 carbon atoms;

$R_1$ is selected from hydrogen, a methyl group, a phenyl group optionally substituted with alkyl having 1 to 6 carbon atoms, a phenylalkyl group the alkyl of which has 1 to 4 carbon atoms; and $R_2$ is selected from hydrogen, a methyl group, or a fluoromethyl group.

The compounds of formula 1 of the present invention are useful starting materials for the manufacture of a number of pharmaceutically active compounds such as mirtazepine, sparfloxacin, cetirizine, cinnarizine, oxatomide, clozapine and olanzapine.

Piperazine is generally prepared by treating ammonia with ethylenediamine (SU467073), aminoethylethylenediamine (SU427936), monoethanolamine (CN1106000) or diethanolamine (JP58035179); or hydrogenation of N-(aminoethyl)ethanolamine (JP49010513). However, all these processes require high temperature and pressure, and give mixtures making isolation of piperazine difficult.

C. B. Pollard et al in J. Med. Chem. 9, 181–185 (1966) report the preparation of 2-phenylpiperazine starting from α-halophenyl acetic acid ester and ethylenediamine which resulted in the formation of 2-keto-3-phenylpiperazine of formula 2. Further, reduction of the compound of formula 2 with lithium aluminum hydride provides 2-phenylpiperazine of formula 3. The drawback of this method is that the reaction between α-halophenyl acetic acid ester and ethylenediamine gives a polymeric mixture which poses difficulty in isolating the pure compound of formula 2.

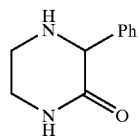

2

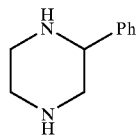

3

WO 98/08826 teaches the preparation of 2-arylpiperazines from 2-halopyrazine by reaction with an aryl Grignard reagent followed by reduction by hydrogenation in the presence of palladium acetate. The Grignard reaction is not facile as it yields 39% product and further requires the use of expensive catalyst, viz., [1,2 bis (diphenylphosphino) ethane] nickel (II) chloride in high quantity.

U.S. Pat. No. 4,912,110 discloses a process for the preparation of a compound of formula 4.

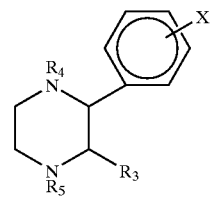

4 wherein:
$R_3$ is H or a $C_1$ to $C_2$ alkyl group,
$R_4$ is H or a $C_1$ to $C_4$ alkyl group,
$R_5$ is H or a $C_1$ to $C_4$ alkyl group and
X is H, F, Cl or Br,
at least one of the symbols $R_3$, $R_4$, $R_5$ and X being different from H.

The process of preparation recommended in U.S. Pat. No. 4,912,110 consists in

A. reacting a 1-phenylalkane-1,2-dione of the formula 5 with ethylenediamine to give 2-phenyldihydropyrazine of the formula 6 wherein X and $R_3$ are as defined above;

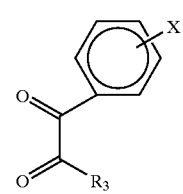

5

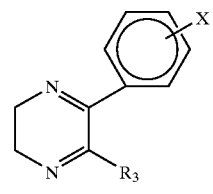

6

B. subjecting the resulting compound of the formula 6 (where $R_3$ and X=H) to a reduction reaction with a reducing agent, selected especially from the group consisting of, $LiAlH_4$ and $NaBH_4$, to give 2-phenylpiperazine of the formula 3; and C. if necessary, subjecting the resulting compound of the formula 3 to an alkylation reaction in order to introduce the group $R_3=C_1$ to $C_2$ alkyl or the groups $R_4$ and $R_5$ in formula 4 each representing a $C_1$ to $C_4$ alkyl group.

However, the yields of this process are very low. Typically, an overall yield of 6% is obtained for 1-isopropyl-2-methyl-3-phenylpiperazine starting from 1-phenylpropane-1,2-dione.

This patent also suggests that reaction of 1-phenylalkane-1,2-dione of the formula 5 with a monoalkyl ethylenediamine of the formula 7 wherein R and $R_2$ are as defined above, gives phenylpiperazine compounds of formula 8a instead of compounds of the present invention having formula 8b.

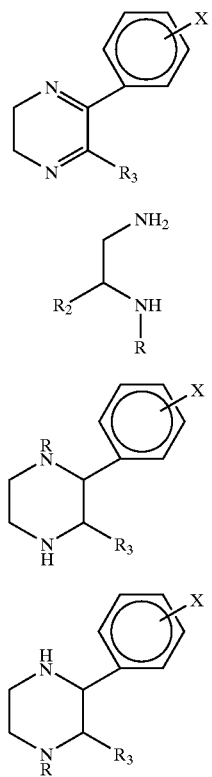

Further, the patent also discloses that N-alkylation of piperazine is carried out in the presence of an alkyl halide and when the alkyl halide is an alkyl iodide, like $ICH_3$, 8b ($R=CH_3$) instead of 8a ($R=CH_3$) is the favored product.

WO 98/08826 describes the reaction of 2-phenylpiperazine 3 with 3,5-bis(trifluoromethylbenzylbromide) to furnish the corresponding 1-alkyl-3-phenylpiperazine. The drawback of this process is that it is carried out at a very low temperature of −78° C.

U.S. Pat. No. 4,772,705 discloses the preparation of 1-methyl-3-phenylpiperazine from 2-phenylpiperazine, using methyl iodide as the methylating agent. However, the yield is low (54%) and the reaction requires low temperature conditions (0° C.) for selective alkylation at the 1-position.

Also, when the alkylation is performed with methyl iodide on 2-phenylpiperazine 3 (as described by V. M. Dixit et al in Indian Journal Of Chemistry Vol.14B, November 1976, pp 874–878), a mixture of products is obtained, viz., the desired 1-methyl-3-phenylpiperazine 1 (where $R=CH_3$, $R_1=Ph$ and $R_2=H$), unreacted 2-phenylpiperazine 3,1-methyl-2-phenylpiperazine 9, and 1,4-dimethyl-2-phenylpiperazine 10.

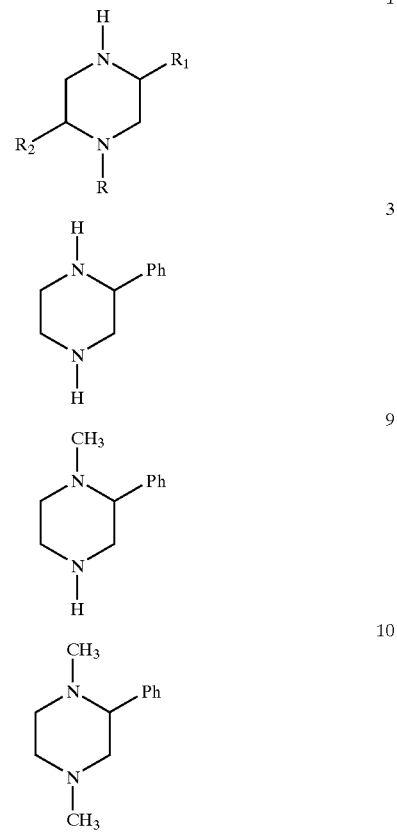

N-methylpiperazine can be prepared by reacting formaldehyde with aminoethylethanolamine in the presence of hydrogen over a metallic hydrogenation-dehydrogenation catalyst, as disclosed in U.S. Pat. No. 5,414,087. The method taught in this patent requires use of an expensive catalyst like nickel-copper-chrome.

All of the foregoing patents and publications are incorporated herein by reference.

SUMMARY OF THE INVENTION

The principal object of the present invention is to provide a simple and efficient process for preparation of piperazine and its derivatives of the aforesaid formula 1.

A further object of the present invention is to provide a simple and efficient process for the preparation of 1-alkyl-3-phenylpiperazine without the need for alkylation of 2-phenylpiperazine and subsequent formation of 1-alkyl-2-phenylpiperazine and 1,4-dialkyl-2-phenylpiperazine as side products.

Thus the present invention is for a method for the preparation of piperazine and its derivatives of formula 1,

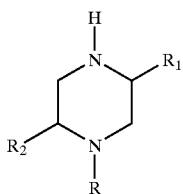

wherein R is selected from hydrogen, or a lower alkyl group having 1 to 6 carbon atoms or a phenylalkyl group the alkyl of which has 1 to 4 carbon atoms;

$R_1$ is selected from hydrogen, a methyl group, a phenyl group optionally substituted with alkyl having 1 to 6 carbon atoms, a phenylalkyl group the alkyl of which has 1 to 4 carbon atoms; and $R_2$ is selected from hydrogen, a methyl group, or a fluoromethyl group and wherein the method comprises the steps:

a. reacting an ester of formula 11 with substituted or unsubstituted ethylenediamine 7 to give 3,4-dehydropiperazine-2-one and its derivatives of formula 12

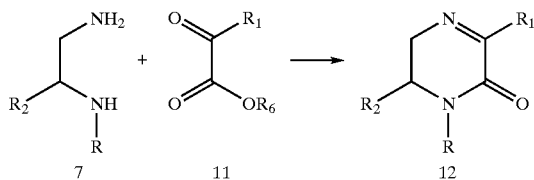

wherein R, $R_1$, $R_2$ are as defined above and
$R_6$ is a $C_1$ to $C_4$ linear or branched alkyl group; and b. reacting the 3,4-dehydropiperazine-2-one and its derivatives of formula 12 thus obtained with a reducing agent to yield piperazine and its derivatives of formula 1.

In a preferred embodiment of the present invention, the piperazine derivative of formula 1 is 1-methyl-3-phenylpiperazine.

DETAILED DESCRIPTION (A) Step (a): Preparation of Compounds of Formula 12

The process of the present invention uses a novel methodology the first step comprising reacting an ester of formula 11 with substituted or unsubstituted ethylenediamine 7 to give 3,4-dehydropiperazine-2-one and its derivatives of formula 12, where R, $R_1$, $R_2$ and $R_6$ are as defined above.

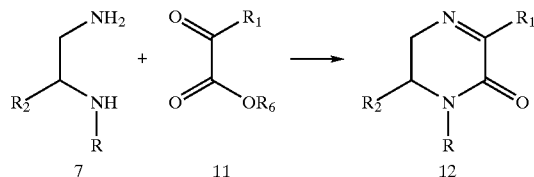

The starting material of formula 7 is ethylenediamine when R and $R_2$ are both hydrogen. The starting material of formula 7, when R and $R_2$ are as defined above, may be prepared by reacting alkyl or phenylalkyl amine with 2-chloroethyl amine hydrochloride or its derivatives followed by neutralization with an alkali.

According to the process of the present invention step (a) is carried out in the presence of an organic acid, a cation exchange resin, or a mineral acid. The organic acid that is preferably employed is an alkyl, an aryl sulphonic acid, or a $C_1$ to $C_{16}$ carboxylic acid. The organic acid is preferably acetic acid.

Examples of cation exchange resins which may be used in step (a) of the process of the present invention are polystyrene-sulfonate resins like Ionac C-250H (available from Sybron Chemicals Inc.), Amberlite IR-120H or IR-122H (available from Rohm and Haas), Resintech CG10-H (available from Resintech) or Dow HCES-H or HGR-H (available from Dow Chemicals).

The mineral acid used in step (a) is preferably selected from the group consisting of hydrochloric acid, sulphuric acid, phosphoric acid, perchloric acid or nitric acid.

In step (a), preferably from 0.1 to 10.0 moles of acid are added for 1 mole of substituted or unsubstituted ethylenediamine. More preferably, 0.5 to 2.0 moles of acid are added for 1 mole of substituted or unsubstituted ethylenediamine. Most preferably however, 1 mole of acid is added for 1 mole of substituted or unsubstituted ethylenediamine.

The reaction between the monoalkyl ethylenediamine of formula 7 and the ester of formula 11 is preferably carried out in an inert solvent in which the reactants are soluble. Examples of the solvents that can be employed are $C_1$ to $C_6$ alcohols, such as ethanol or i- or n-propanol, or hydrocarbons, such as toluene, xylene, benzene, or methylene chloride. The most preferred solvents are alkanols and aromatic hydrocarbons with a boiling range between 60 to 120° C.

Preferably, the reaction is carried out at reaction temperatures of between about 60 and 120° C. The esters of formula 11 employed in the above reaction include those wherein the alkyl residue is $C_1$ to $C_6$, alkyls which are linear, branched or cyclic alkyls, the preferred ones being $C_1$ to $C_4$, and alkyls like methyl, ethyl, isopropyl, cyclopropyl and tertiary butyl, the most preferred alkyls being methyl and ethyl.

(B) Step (b) Reduction of Compounds of Formula 12 to Piperazine and its Derivatives of Formula 1:

In step (b), 3,4-dehydro-piperazine-2-one and its derivatives of formula 12 are reacted with a reducing agent to yield piperazine and its derivatives of formula 1. The reducing agents that may be used include lithium aluminum hydride ($LiAlH_4$), sodium borohydride ($NaBH_4$), aluminum hydride ($AlH_3$), potassium borohydride ($KBH_4$) or borane ($B_2H_6$) using standard conditions to produce piperazine and its derivatives of formula 1.

In step (b), preferably 1-methyl-3-phenyl-3,4-dehydropiperazine-2-one of formula 12 (where R=$CH_3$ and $R_1$=Ph)

is reduced with LiAlH₄ to yield 1-methyl-3-phenylpiperazine of formula 1 (where R=CH₃, R₁=Ph and R₂=H). If desired, the 1-methyl-3-phenylpiperazine of formula 1 is further converted to 1,2,3,4,10,14b-hexahydro-2-methyl-pyrazino [2,1-a]pyrido {2,3-c} [2]benzazepine of formula 17.

17

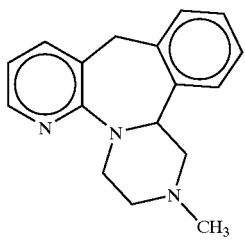

This compound of formula 17 is preferably prepared by the steps comprising (a) reacting 1-methyl-3-phenylpiperazine of formula 1 with 2-chloro-3-cyanopyridine of formula 13 to give 1-(3-cyanopyridyl-2-)-4-methyl-2-phenylpiperazine of formula 14;

13

14

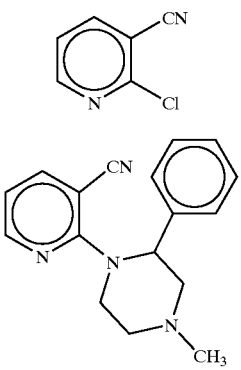

(b) hydrolyzing the compound of formula 14 to give 1-(3-carboxypyridyl-2-)-4-methyl-2-phenylpiperazine of formula 15;

15

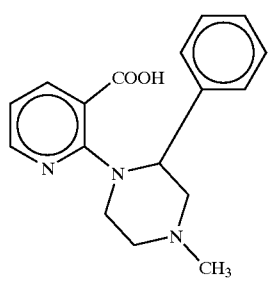

(c) reducing the compound of formula 15 to give 1-(3-hydroxymethylpyridyl-2-)-4-methyl-2-phenylpiperazine of formula 16; and

16

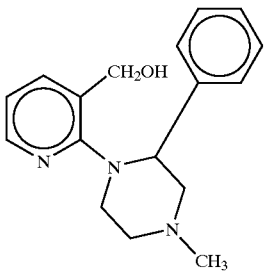

(d) cyclizing the compound of formula 16 to give 1,2,3,4,10,14b-hexahydro-2-methyl-pyrazino[2,1-a]pyrido {2,3-c}[2]benzazepine of formula 17.

17

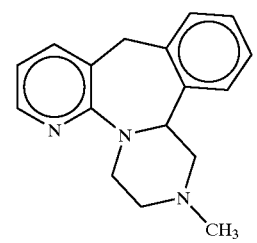

1,2,3,4,10,14b-hexahydro-2-methyl-pyrazino[2,1-a] pyrido {2,3-c} [2]benzazepine of formula 17 is mirtazepine, a useful antidepressant. Methods of preparing mirtazepine from 1-methyl-3-phenylpiperazine are disclosed in U.S. Pat. No. 4,062,848, which is incorporated herein by reference.

Reduction of the compound of formula 15 to the compound of formula 16 (step (c)) may be effected with a metal hydride selected from lithium aluminum hydride, sodium borohydride, aluminum hydride, potassium borohydride and diborane, or by means of catalytic hydrogenation.

The step of cyclization (step (d)) may be carried out under strongly dehydrating conditions such as elevated temperature, or by addition of an acid selected from sulphuric acid, concentrated hydrochloric acid, picric acid, trifluoroacetic acid, phosphoric acid, polyphosphoric acid (PPA), phosphorous oxychloride, phosphorous trioxide, phosphorous pentoxide and Lewis acids, such as aluminum chloride, ferric chloride, zinc chloride, tin chloride, titanium chloride, boron trifluoride, antimony pentachloride or zirconium tetrachloride.

Piperazine and its derivatives of formula 1, are useful intermediates for a number of pharmaceutically active compounds, such as the antidepressant mirtazepine, the antibacterial sparfloxacin, antihistamines such as cetirizine, cinnarizine, and oxatomide, and antipsychotics such as clozapine and olanzapine.

Particularly important starting materials produced by the present invention are 1-methyl-3-phenylpiperazine for making mirtazepine, and cis 2,6-dimethylpiperazine for making sparfloxacin.

The invention is illustrated but not restricted by the description in the following examples:

EXAMPLE-1
Preparation of N-methyl Ethylenediamine of Formula 7 (R=CH$_3$)

To the stirred solution of 40% w/w methylamine (836.6 gms, 10.77 mol) in water, was added 2-chloroethylamine hydrochloride (250.0 gms, 2.155 mol) at room temperature. The reaction mixture was transferred to an autoclave and heated to 100° C. temperature for 6–7 hrs. After completion of the reaction, excess methylamine gas was released and to the mixture was added with stirring solid potassium hydroxide (1.2 kg) at ambient temperature. The organic layer was separated and dried over solid potassium hydroxide (50.0 gms). The dried organic layer was decanted to get crude product which was distilled under vacuum (10–15 mm) at 38°–45° C. to get N-methyl ethylenediamine of formula 7 (69.0 gms, 43.1% yield) as a pale yellow liquid.

EXAMPLE-2
Preparation of 1-Methyl-3-phenyl-3,4-dehydropiperazine-2-One of Formula 12 (R=CH$_3$, R$_1$=Phenyl):

To a solution of N-methyl ethylenediamine (1.085 g, 14.6 mmol) in methanol (15 ml) was added acetic acid (0.878 g, 14.6 mmol) at 30–32° C., followed by a solution of methyl benzoylformate (2.0 g, 12.2 mmol) in methanol (5 ml). The mixture was stirred at 30–32° C. for 7 hrs. The solvent was removed under vacuum at 40–45° C., to the residue was added toluene (20 ml) and stirred for 15 min. to get a clear solution. Toluene layer was washed with 10% acetic acid solution (5 ml) followed by saturated brine solution (2×5 ml). The toluene layer was dried over anhydrous sodium sulphate and the solvent was removed under vacuum. To the residue obtained was added hexane (12 ml) and stirred for 30 mins. The precipitated solid was filtered and dried under vacuum to yield 1-methyl-3-phenyl-3,4-dehydropiperazine-2-one 12 (1.10 g, yield 48%).

EXAMPLE-3
Preparation of 1-Methyl-3-phenyl-3,4-dehydropiperazine-2-One of Formula 12 (R=CH$_3$, R$_1$=Phenyl):

To a solution of N-methyl ethylenediamine (5.64 kg, 76.15 mol) in toluene (80 L) was added glacial acetic acid(4.56 kg, 76.15 mol) at 20–22° C. To the stirred reaction mixture was added methyl benzoylformate (10.0 kg, 60.91 mol) and stirred for 15 min. at 30–35° C. The reaction mixture was slowly heated to 60–65° C., and maintained at that temperature for 6 hrs. The reaction mixture was cooled to ambient temperature and the aqueous lower layer was separated. The upper organic layer was washed with 2% acetic acid (2×5 lt.) followed by water (5.0 L). The toluene layer containing product was concentrated under vacuum at 60–65° C. To the crude residue obtained, hexane was added (50 L) and stirred for 3.0 hrs at ambient temperature. The solid precipitate was filtered and dried under vacuum to obtain 1-methyl-3-phenyl-3,4-dehydropiperazine-2-one 12. (7.98 kg, yield 69.6%, m.p.56–60° C.)

EXAMPLE-4
Preparation of 1-Methyl-3-phenylpiperazine of Formula 1 (R=CH$_3$):

Lithium aluminum hydride (LiAlH$_4$) solid (193.8 g, 5.1 mol) was added in portions to a solution of THF (2.88 L) under nitrogen atmosphere. To the LiAlH$_4$ suspension was added 1-methyl-3-phenyl-3,4-dehydropiperazine-2-one 12 (480.0 g, 2.55 mol) in THF (0.96 L) at 10–15° C. The reaction mixture was heated to 50–55° C. for 3–4 hrs. After completion of the reaction, the reaction mixture was cooled to 15–20° C. and ethyl acetate (200 ml) was added and stirred for 30 mins followed by water (194 ml). To the resultant thick slurry was added ethyl acetate (300 ml) and sodium hydroxide solution (15.0%,194 ml) and stirred for 30 min. To the stirred solution at 15–20° C. was added water (582 ml) and stirred for 1.5 hrs. The inorganic solids were filtered, the solid bed was washed with ethyl acetate, and the combined organic layer was concentrated under vacuum to furnish oily product. To the oil was added hexane (2.4 L) refluxed for 1.0 hr, and treated with charcoal and filtered. The filtrate was concentrated under vacuum to obtain 1-methyl-3-phenylpiperazine 1 (272 g, yield 60.5%)

EXAMPLE-5
Preparation of 1,2,3,4,10,14b-hexahydro-2-methyl-pyrazino[2,1-a] pyrido{2,3-c} [2]Benzazepine of Formula 17:

1-Methyl-3-phenylpiperazine (50.0 g, 0.284 mol) was heated with 2-chloro-3-cyanopyridine (39.35 g, 0.284 mol) in the presence of potassium fluoride (49.51 g, 0.852 mol) and N,N-dimethylformamide (750.0 ml) as a solvent for 30.0 hrs at 148–154° C., followed by quenching with water and extraction with ethyl acetate gave 1-(3-cyanopyridyl-2-)-4-methyl-2-phenylpiperazine (70.0 g). 1-(3-Cyanopyridyl-2)-4-methyl-2-phenylpiperazine on hydrolysis with saturated alcoholic potassium hydroxide solution (850.0 ml) at 80–85° C. followed by extraction with chloroform gave 1-(3-carboxypyridyl-2)-4-methyl-2-phenylpiperazine (20.0 g). The acid obtained, 1-(3-carboxypyridyl-2)-4-methyl-2-phenylpiperazine (20.0 g, 0.067 mol), was reduced with lithium aluminum hydride (20.0 g, 0.536 mol) in tetrahydrofuran (1.0 L) to give 1-(3-hydroxymethylpyridyl-2)-4-methyl-2-phenylpiperazine (16.5 g, 80.0% yield). An alcohol derivative, 1-(3-hydroxymethylpyridyl-2)-4-methyl-2-phenylpiperazine (16.0 g, 0.056 mol), upon treatment with sulphuric acid (60.0 g, 0.61 mol) at room temperature followed by extraction with dichloromethane, yields the final crude product. The crude product obtained is recrystallized and charcoalized from n-hexane to get 1,2,3,4,10,14b-hexahydro-2-methyl-pyrazino[2,1-a]pyrido{2,3-c} [2]benzazepine (8.25 g, 55.0% yield).

We claim:
1. A method for the preparation of piperazine and its derivatives of formula 1,

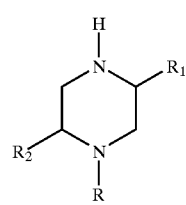

wherein R is selected from hydrogen, a lower alkyl group having 1 to 6 carbon atoms or a phenylalkyl group the alkyl of which has 1 to 4 carbon atoms;

R$_1$ is selected from hydrogen, a methyl group, a phenyl group optionally substituted with an alkyl group having 1 to 6 carbon atoms, or a phenylalkyl group the alkyl of which has 1 to 4 carbon atoms; and $R_2$ is selected from hydrogen, a methyl group, or a fluoromethyl group; wherein the method comprises the steps:
  a. reacting an ester of formula 11 with substituted or unsubstituted ethylenediamine of formula 7 to give a 3,4-dehydropiperazine-2-one and its derivatives of formula 12

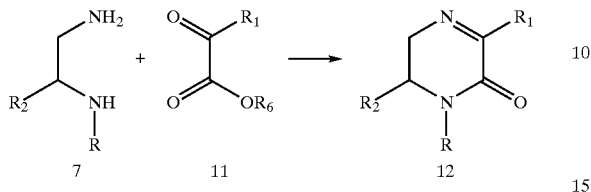

wherein R, $R_1$, $R_2$ are as defined above and
  $R_6$ is a $C_1$ to $C_4$ linear or branched alkyl group; and
  b. reacting the 3,4-dehydro-piperazine-2-one and its derivatives of formula 12 thus obtained with a reducing agent to yield piperazine and its derivatives of formula 1.

2. A process as claimed in claim 1 wherein the piperazine derivative of formula 1 is 1-methyl-3-phenylpiperazine.

3. A process as claimed in claim 1 wherein step (a) is carried out in the presence of an organic acid, a cation exchange resin or a mineral acid.

4. A process as claimed in claim 3 wherein the organic acid is an alkyl or an aryl sulphonic acid, or a $C_1$ to $C_{16}$ carboxylic acid.

5. A process as claimed in claim 3 wherein the organic acid is acetic acid.

6. A process as claimed in claim 3 wherein the mineral acid is selected from the group consisting of hydrochloric acid, sulphuric acid, phosphoric acid, perchloric acid, and nitric acid.

7. A process as claimed in claim 3 wherein 0.1 to 10.0 moles of the organic or mineral acid is present for each mole of the ethylenediamine of formula 7.

8. A process as claimed in claim 7 wherein 0.5 to 2.0 moles of the acid is present for each mole of the ethylenediamine of formula 7.

9. A process as claimed in claim 8 wherein 1 mole of the acid is present for each mole of the ethylenediamine of formula 7.

10. A process as claimed in claim 1 wherein the ethylenediamine of formula 7 is prepared by reacting a corresponding lower alkyl group having 1 to 6 carbon atoms or a phenylalkyl the alkyl of which has 1 to 4 carbon atoms, with 2-chloroethylamine hydrochloride or its derivative followed by neutralization with an alkali.

11. A process as claimed in claim 1 wherein the piperazine of formula 1 is 1-methyl-3-phenylpiperazine which is further converted to 1,2,3,4,10,14b-hexahydro-2-methyl-pyrazino[2,1-a]pyrido{2,3-c} [2]benzazepine of formula 17

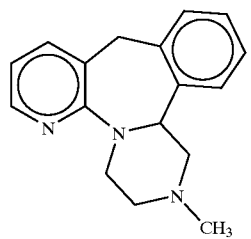

by the steps comprising:
  (a) reacting the 1-methyl-3-phenylpiperazine of formula 1 with 2-chloro-3-cyanopyridine of formula 13 to give 1-(3-cyanopyridyl-2-)-4-methyl-2-phenylpiperazine of formula 14;

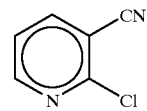

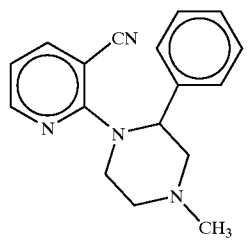

(b) hydrolyzing the compound of formula 14 to give 1-(3-carboxypyridyl-2-)-4-methyl-2-phenylpiperazine of formula 15;

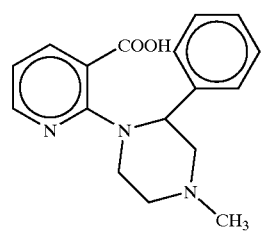

(c) reducing the compound of formula 15 to give 1-(3-hydroxymethylpyridyl-2-)-4-methyl-2-phenylpiperazine of formula 16; and

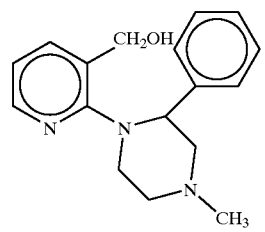

(d) cyclizing the compound of formula 16 to give 1,2,3,4,10,14b-hexahydro-2-methyl-pyrazino[2,1-a]pyrido{2,3-c} [2]benzazepine of formula 17;

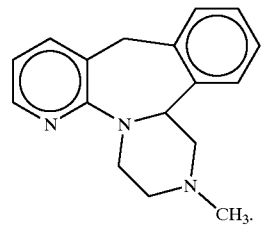

* * * * *